United States Patent [19]
Deigin et al.

[11] Patent Number: 6,103,699
[45] Date of Patent: Aug. 15, 2000

[54] PEPTIDE, A METHOD FOR ITS PREPARATION AND A PHARMACEUTICAL COMPOSITION CONTAINING THE PEPTIDE

[75] Inventors: Vladislav I. Deigin, North York, Canada; Andrei Marxovich Korotkov, Moscow, Russian Federation

[73] Assignee: Immunotech Developments Inc., Toronto, Canada

[21] Appl. No.: 09/032,550

[22] Filed: Feb. 26, 1998

Related U.S. Application Data

[63] Continuation-in-part of application No. 08/657,888, Jun. 7, 1996, Pat. No. 5,736,519.

[51] Int. Cl.[7] .......................... A61K 38/00; A61K 38/05; A61K 38/06; A61K 38/07
[52] U.S. Cl. ................................. 514/18; 514/19; 930/21
[58] Field of Search ......................................... 514/18, 19

[56] References Cited

U.S. PATENT DOCUMENTS

| | | | |
|---|---|---|---|
| 4,959,455 | 9/1990 | Clark et al. | 530/351 |
| 4,999,291 | 3/1991 | Souza | 435/69.1 |
| 5,278,145 | 1/1994 | Keller et al. | 514/12 |

FOREIGN PATENT DOCUMENTS

| | | |
|---|---|---|
| 29308/89 | 1/1989 | Australia . |
| 331934 | 9/1989 | European Pat. Off. . |
| WO88/05469 | 7/1988 | WIPO . |
| WO 92/09628 | 6/1992 | WIPO . |
| WO 93/08815 | 5/1993 | WIPO . |

OTHER PUBLICATIONS

Semina et al. (Radiatsionnaya Biologiya Radioekologiya 33(3):808–811, 1993 (Abstract).

*Primary Examiner*—Cecilia Tsang
*Assistant Examiner*—Michael Borin
*Attorney, Agent, or Firm*—Merchant & Gould P.C.

[57] ABSTRACT

A peptide of the formula I

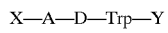

wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid or ξ-aminocaproic acid; A is D-gluptamic acid or D-iso-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophn, γ-aminobutyric acid, ξ-aminocaproic acid, hydroxyl, or an amide group.

7 Claims, 2 Drawing Sheets

PEPTIDE, A METHOD FOR ITS PREPARATION AND A PHARMACEUTICAL COMPOSITION CONTAINING THE PEPTIDE

This application is a continuation-in-part of United States application Ser. No. 08/657,888 that was filed on Jun. 7, 1996, now U.S. Pat. No. 5,736,519.

FIELD OF THE INVENTION

The invention relates to novel immunosuppressive peptides; novel pharmaceutical compositions containing the peptides; and therapeutic uses of the peptides.

BACKGROUND TO THE INVENTION

Radiotherapy and chemotherapy are well-established treatment methods for malignant disease. Cells, which grow and divide rapidly, are most vulnerable to the effects of radiation and cytotoxic agents. Among those effected are tumor cells, and normal cells including hair and intestinal cells, and cells of the hemopoietic and immune systems. Damage to normal cells of the hemopoietic and immune systems by radiation and cytotoxic agents often has life-threatening consequences, and it limits the ability to administer a full therapeutic dose.

There has been extensive research to identify agents which will protect normal hemopoietic and immunologic cells from the effects of radiotherapy and chemotherapy, or aid in the reconstitution of cells suppressed by these therapies. For example, transforming growth factor beta-1 has been reported to be useful for protecting hematopoietic stem cells from the myelotoxicity of chemotherapeutic drugs or radiation therapy (U.S. Pat. No. 5,278,145 to Keller et al.) A lyophilised composition containing human albumin in thymosin alpha 1 was also reported to exert a preventative activity against progression of leukaemia's in mice whose immune systems were severely damaged by treatment with cytostatic agents or radiation treatment (89EP 102569 to Lattanzi). Hemopoietic growth factors such as interleukin-3 and CSF have been used to potentiate immune response or assist in reconstituting normal blood following radiation-or-chemotherapy-induced hematopoietic cell suppression (WO8805469 to Anderson et al., U.S. Pat. No. 4,959,455 to Ciarletta et al; U.S. Pat. No. 4,999,291).

Semina et al. (Radiatsionnaya Biologiya Radioekologiya 33(3), 1993; WO 8906134) have shown that the levorotary (L) enantiomer of the dipeptide H-Glu-Trp-OH acts as an immunostimulant and can induce the proliferation of cells. As such, these dipeptides are useful in reconstituting hemopoietic and immune cells after chemotherapy or irradiation therapy.

SUMMARY OF THE INVENTION

The inventors have surprisingly found that the dextrorotary (D) enantiomers of the peptides of the present invention have the opposite activity as compared to their L-enantiomeric counterparts.

In particular, the inventors have found that the D enantiomers of the peptides are immunosuppressive and inhibit the proliferation of cells. In contrast, the corresponding L-enantiomers are immunostimulants and induce the proliferation of cells. Consequently, the peptides of the present invention are useful in protecting cells from the damaging effects of irradiation and chemotherapy. Both irradiation and chemotherapy act on rapidly proliferating or dividing cells (i.e cells in S-phase) while the peptides of the present invention inhibit the proliferation of the cells (i.e. cells in G-phase) thereby making the cells resistant to the damaging effects of the radiation or chemotherapy. The protected cells can then be induced to proliferate (or reconstitute) using agents known in the art such as the L-peptides described by the inventor in his co-pending application Ser. No. 08/894, 963 which is incorporated by reference in its entirety.

Broadly stated, the present invention relates to a peptide of formula I

X—A—D—Trp—Y  (I)

wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, or ξ-aminocaproic acid; A is D-glutamic acid, or D-iso-glutamic acid; D-iGlu and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, ξ-aminocaproic acid, hydroxyl or an amide group.

In a preferred embodiment, the present invention relates to the peptide H-D-iGlu-Trp-OH or H-D-Glu-D-Trp-OH.

The invention also relates to analogues of the peptides of the invention and cyclic peptides. The terms "peptide" and "peptides" used to herein include these analogues and cyclic peptides.

The invention also contemplates a method for preparing the peptides. The method should result in good yield of the product using simple and efficient steps.

The peptides of the invention have many therapeutic applications. In particular, the peptides of the invention can be used whenever it is desirable to inhibit cell proliferation. Accordingly, in one embodiment, the present invention relates to a method of inhibiting cell proliferation comprising administering an effective amount of a peptide of the invention to a cell or animal in need thereof.

In another embodiment, the present invention relates to a method of ameliorating graft survival comprising administering an effective amount of a peptide of the invention to an animal in need thereof.

In a further embodiment, the present invention relates to a method of protecting cells during hyperthermia comprising administering an effective amount of a peptide of the invention to an animal in need thereof.

The peptides of the invention have been shown to be non-toxic and to protect the cells of the hemopoietic and immune systems when the cells are exposed to radiation or chemotherapeutic agents. Accordingly, in another embodiment, the invention relates to a method of protecting cells of the hematopoietic and immune systems in an animal during radiation or chemotherapy comprising administering an effective amount of a peptide of the invention to an animal in need thereof.

In yet another embodiment, the invention also relates to a method of immunosuppressing an immune system in an animal comprising administering an effective amount of a peptide of the invention to an animal in need thereof. In one embodiment, the peptide may be administered prior to an organ or bone marrow transplant.

The present invention also includes a pharmaceutical composition comprising one or more peptides of the invention and a pharmaceutically acceptable carrier.

Additional objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the detailed description.

DETAILED DESCRIPTION OF THE PREFERRED EMBODIMENT

Figure 1:
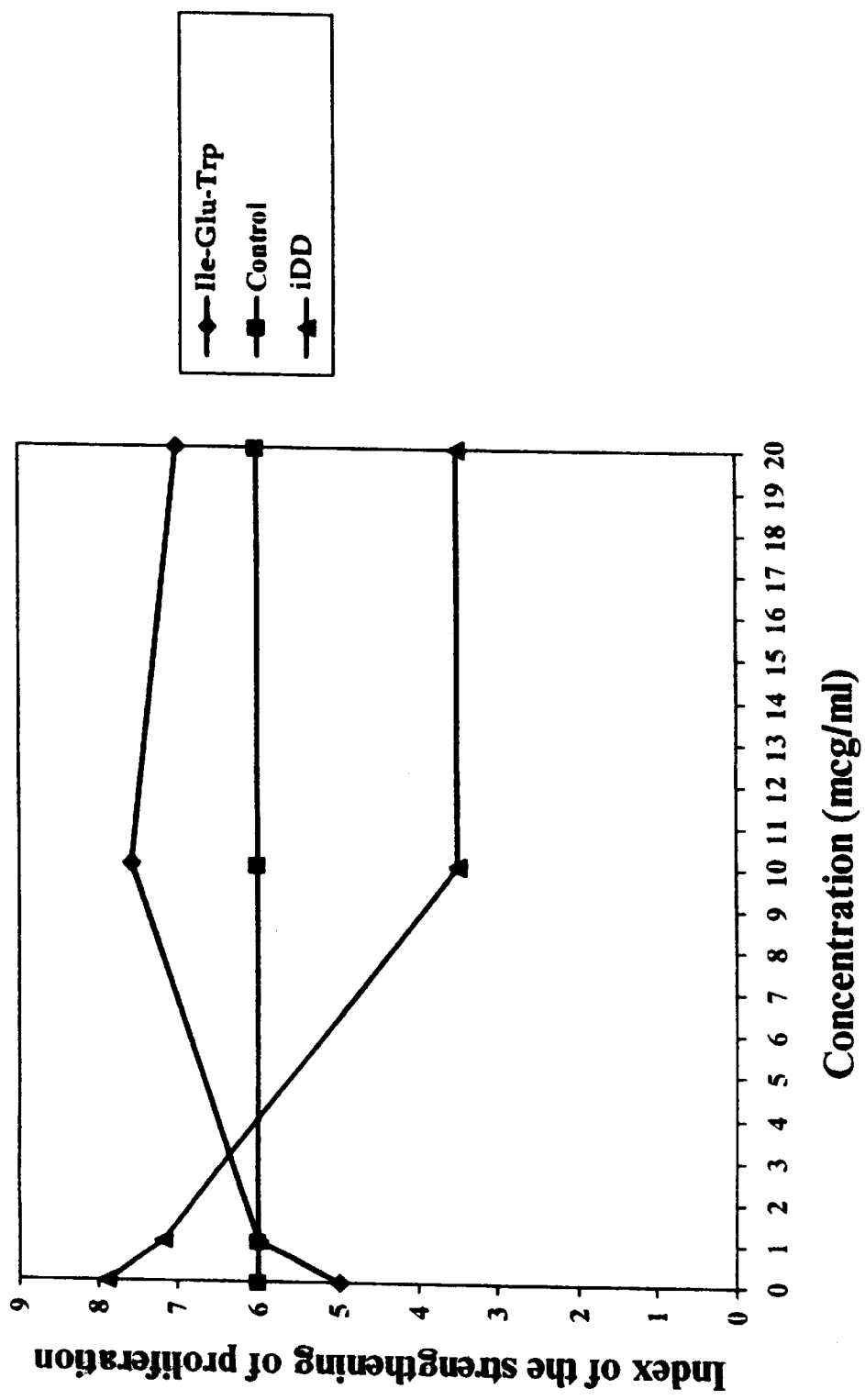
FIG. 1 is a graph showing the effect of various peptides on cell proliferation.

The following standard abbreviations for the amino acid residues are used throughout the specification: Ala—alanine; Glu—glutamic acid; iGlu—iso-glutamic acid; Phe—phenylalanine; Gly—glycine; le—isoleucine; Leu—leucine; Pro—proline; Val—valine; Nval—N-valine; Trp—tryptophan; and Tyr—tyrosine.

As mentioned previously, the present invention relates to a peptide of formula I

X—A—D—Trp—Y    (I)

wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, ξ-aminocaproic acid; A is D-glutamic acid or D-iso-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, ξ-aminocaproic acid, hydroxyl or an amide group.

In an embodiment of the invention, in the peptide of the formula I, X is hydrogen, A is D-glutamic acid or D-iso-glutamic acid, and Y is OH or an amide. The amide may be substituted with an alkyl group including methyl, dimethyl, ethyl, or 1, 1-methyl, ethyl groups as follows:

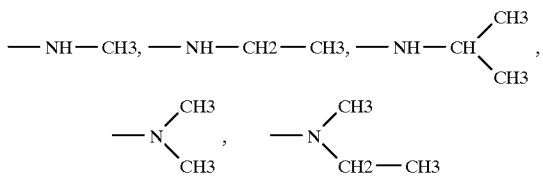

Preferred peptides of the invention have the sequence H-D-Glu-D-Trp-OH and H-D-iGlu-Trp-OH (also referred to as "iDD").

The peptides of the invention may additionally be characterised by the following physical and chemical properties: a yellowish-white or grey powder, soluble in water, moderately soluble in alcohol, and insoluble in chloroform. The UV spectrum is the range of 250–300 nm has a maximum at 280±2 nm, and a shoulder at 287±2 nm.

The peptides of the invention may also include analogues of the peptide of Formula I which may include, but are not limited to the peptide of Formula I containing one or more amino acid insertions. Amino acid insertions may consist of a single amino acid residue or sequential amino acids. Analogues of the peptide of the invention exhibit the activity of the peptide and may further possess advantageous features such as increased bioavailability, stability, or reduced host immune recognition.

The invention includes cyclic derivatives of the peptides of the invention. Cyclization allows the peptide to assume a more favourable conformation. Cyclization of the peptides may be achieved using techniques known in the art. In particular, disulphide bonds may be formed between two appropriately spaced components having free sulfhydryl groups. The bonds may be formed between side chains of amino acids, non-amino acid components or a combination of the two.

Peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

The peptides of the invention may be synthesised by preparing the glutamyl containing peptides in solution by opening the internal anhydride of tertbutyloxycarbonyl-glutamic (D or L) acid using the corresponding D-Trp-Y derivative, followed by chromatographic separation of α-and γ-isomers, and further chain building with the use of activated esthers or mixed anhydrides of protected amino acids.

Boc-Glu-OH is introduced into the reaction with the help of a condensing agent (generally, dicyclohexylcarbodiimide), which, in a water-free medium, helps form the internal anhydride of Boc-glutamic acid. After a nucleophilic agent (an amino acid or a derivative thereof) is added, the reaction of cycle opening takes place with formation of the Boc-Glu- and Boc-iGlu- dipeptides. Then the Boc-groups are removed and the target products, glutamyl- and isoglutamyl- dipeptides, are chromatographically separated and purified.

The method of preparation of the peptides will be better understood in light of the examples discussed later herein.

The peptides of the present invention may also be prepared by chemical synthesis using techniques known in the chemistry of proteins such as solid phase synthesis (for example see Merrifield, 1964, J. Am. Chem. Assoc. 85:2149–2154), and purified by HPLC of protected peptides.

The peptides of the invention have many therapeutic applications. In particular, the peptides of the invention can be used whenever it is desirable to inhibit cell proliferation. Accordingly, in one embodiment, the present invention relates to a method of inhibiting cell proliferation comprising administering an effective amount of a peptide of the invention to a cell or animal in need thereof.

In another embodiment, the present invention relates to a method of ameliorating graft or transplant survival comprising administering an effective amount of a peptide of the invention to an animal in need thereof. The present inventor has also found that the peptide of the invention increased the survival of animals receiving allogenic bone marrow transplants.

In a further embodiment, the present invention relates to a method of protecting cells during hyperthermia comprising administering an effective amount of a peptide of the invention to an animal in need thereof.

In another embodiment, the invention relates to a method of protecting cells of the hematopoietic and immune systems in an animal during radiation or chemotherapy comprising administering an effective amount of a peptide of the invention to an animal in need thereof. Cells of the hemopoietic and immune systems include stem, myeloid, erythroid, lymphoid, or megacaryocyte cells, or mature myeloid or lymphoid cells, or combinations thereof.

In yet another embodiment, the invention also relates to a method of immunosuppressing an immune system in an animal comprising administering an effective amount of a peptide of the invention to an animal in need thereof. In one embodiment, the peptide may be administered prior to an organ or bone marrow transplant.

The present invention also includes a pharmaceutical composition comprising one or more peptides of the invention and a pharmaceutically acceptable carrier.

The peptides of the present invention may be formulated into pharmaceutical compositions for administration to patients in an effective amount and in a biologically compatible form suitable for in vivo administration, i.e. a form of the peptides to be administered in which any toxic effects are outweighed by the therapeutic effects.

The peptides may be administered to animals preferably humans in a therapeutically effective amount. A therapeutically effective amount is defined as an amount of the active ingredient, i.e., peptide, effective, at dosages and for periods of time necessary to achieve the desired result i.e. protection of cells of the hemopoietic and immune systems. A therapeutically effective amount of a peptide may vary according to factors such as disease state, age, sex, and weight of the individual. Dosage regime may be altered to provide the optimum therapeutic response. Generally, the daily regimen should be in the range of 1–100 μg/kg, preferably 100 μg/kg, of the peptide when treating a non-human animal and in the range of 0.1 g to 10 g/kg when treating a human.

The peptides may be administered by any means known in the art. Because the desired targets of the peptides occur primarily in the bone marrow and blood system it is desirable to reach those tissues. The peptides can be administered either parenterally, intravenously, subcutaneously or intranasally. Depending upon the route of administration, the peptides in the pharmaceutical compositions may be coated in a material to protect them from the action of enzymes. Organic substances may also be included in the compositions to prolong the pharmacological actions of the peptides. Examples of such organic compositions include non-antigenic gelatine, carboxymethylcellulose, sulphonate, or phosphate ester of alginic acid, dextran, polyethylene glycol and other glycols, phytic acid, polyglutamic acid, and protamine.

The pharmaceutical compositions of the invention can be prepared by per se known methods for the preparation of pharmaceutically acceptable compositions which can be administered to subjects, such that an effective quantity of peptide is combined in a mixture with a pharmaceutically acceptable vehicle. Examples of pharmaceutically acceptable vehicles are described in Remington's Pharmaceutical Sciences (Remington's Pharmaceutical Sciences, Mack Publishing Company, Easton, Pa., and USA 1985).

Compositions for injection include, albeit not exclusively, the peptides in association with one or more pharmaceutically acceptable vehicles or diluents, and contained in buffered solutions with a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedures. A certain amount of the peptide is diluted to the necessary volume with a diluent or solvent. The solution is then filtered through sterilised filters, bottled or ampoule. The resultant solution is a stable transparent liquid, and does not contain any chemical or other impurities.

Solid form preparations for oral administration can be made in the form of tablets, powders, or capsules. It may contain a medium for the active substance and other additives, including dyes, aromas, etc.

The compositions and treatments are indicated as therapeutic agents or treatments either alone or in conjunction with other therapeutic agents or other forms of treatment. In particular, the compositions of the invention may be used in combination with radiotherapy or chemotherapy, such as multi-drug chemotherapy or combination radiotherapy, and chemotherapy. The pharmaceutical composition may also be administered in conjunction with other agents which enhance reconstitution of hemopoietic and immune cells such as growth factors and the peptides described by the inventor in U.S. application Ser. No. 08/894,963. Preferably, the peptide of the invention is administered prior to radiation or chemotherapy. Following radiation or chemotherapy the peptide Ile-Glu-Trp is administered which can enhance the proliferation or recovery of the hematopoietic cells.

The following non-limiting examples are illustrative of the present invention.

EXAMPLE 1

Preparation of H-D-iGlu-Trp-OH (iDD)

a) Preparation of Boc-D-Glu-OH 14.7 g (0.1 Mol) of H-D-Glu-OH was dissolved in 200 ml of distilled water, and the pH was adjusted to 10.2 with 0.1M potassium hydroxide. 33.0 g (0.3 Mol) of $BOC_2O$ in dioxane was added with intensive mixing. The pH was controlled using a pH-stat. After completion of the reaction, the mixture was transferred to a separating funnel, and extraction was carried out from the alkaline solution with ethyl acetate (3×150 ml). The pH of the aqueous phase was adjusted to 3.0 using 0.2% sulphuric acid, and Boc-D-Glu-OH was extracted from the organic phase (3×200 ml). The organic phase was washed three times with 200 ml of $Na_2SO_4$ saturated solution to neutral pH, and dried over $Na_2SO_4$, and evaporated to oil under vacuum. The yield was 16.7 g (68%).

b) Preparation of Boc-D-Glu-D-Trp-OH and Boc-iD-Glu-D-Trp-OH mixture 16.7 g (0.068 Mol) Boc-D-Glu-OH was dissolved in 200 ml dimethyl formamide cooled to 0° C., and 20.6 g (0.1 Mol) N,N'-dicyclohexylcarbodiimide in 100 ml dimethyl formamide was added to the solution. The mixture was stirred at 4° C. for 4 h, and then was stored at room temperature for 8 h. The precipitate of dicyclohexyl carbomimide was filtered, and washed twice with 50 ml dimethyl formamide. The filtrate was concentrated by evaporation under vacuum to ½ volume, cooled to 4° C., and to this was added 24.3 g (0.1 Mol) H-D-Trp-OH with vigorous mixing. The solution was allowed to warm to room temperature. Completion of the reaction was carried out by thin layer chromatography (TLC) in a system of chloroform: ethyl acetate: methanol= 6:3:1 by disappearance of the spot internal anhydride of Boc-D-Glu acid. The remaining dicyclohexyl carbodimide was separated by filtration and evaporation under vacuum. The resulting residue was a thick oil. 200 ml ethyl acetate and 200 ml of 0.2% sulphuric acid solution were added to the residue. The organic layer was separated, washed with $Na_2SO_4$ saturated solution to neutral pH, and dried over $Na_2SO_4$. The residue was further dried by evaporation under vacuum. The resultant oil-like precipitate was a mixture of Boc-D-Glu-D-Trp-OH and Boc-D-iGlu-Trp-OH. Total yield of the mixture was 25.4 g (70%).

c) Preparation of H-D-Glu-D-Trp-OH and H-D-iGlu-D-Trp-OH mixture 25.4 g of the Boc-D-Glu-Trp-OH and Boc-D-iGlu-Trp-OH mixture (0.048 Mol) was dissolved in 200 ml of formic acid, and stirred for 1 h at 40° C. The solvent was evaporated under vacuum to a thick oil.

The peptides were separated and purified by ion exchange chromatography in a Sephadex SP-PEA column in a gradient of 0.01–0.2M pyridine acetate buffer. Yield was 5.7 g (35%) of H-D-Glu-D-Trp-OH and 5.7 g (35%) of H-D-iGlu-Trp-OH.

The resulting peptide has the following physical and chemical properties and characteristics:

Primary structure—H-D-iGlu-Trp-OH

Empirical formula—$C_{16}H_{20}N_3O_5$

Molecular weight—334.35

Appearance—yellowish-white or grey powder

Solubility—readily soluble in water, moderately soluble in alcohol, insoluble in chloroform.

UV-spectrum in the range 250–300 nm has the maximum at 280±2 nm and a shoulder at 287±2 nm.

$Rf_1$=0.30 (chloroform-methanol-32% acetic acid= 60:45:20) and $Rf_2$=0.52 (butanol-pyridine-water-acetic acid=5:5:4:1).

EXAMPLE 2

Table 1 presents physical and chemical characteristics of some analogues of the peptide of the formula I, specifically, $Rf_1$ in the system (chloroform:methanol:32% acetic acid= 60:45:20) and $Rf_2$ in the system (butanol:pyridine:water:acetic acid=5:5:4:1).

TABLE 1

| Peptide | $Rf_1$ | $Rf_2$ |
|---|---|---|
| H-D-Glu-D-Trp-OH | 0.36 | 0.56 |
| H-D-iGlu-Trp-OH | 0.30 | 0.52 |
| H-L-iGlu-D-Trp-OH | 0.34 | 0.61 |
| Ala-D-iGlu-D-Trp-OH | 0.32 | 0.55 |
| ξ-aminocaproyl-D-Glu-D-Trp-OH | 0.31 | 0.52 |
| ξ-aminocaproyl-D-iGlu-D-Trp-OH | 0.28 | 0.49 |
| H-D-Glu-D-Trp-Lys | 0.27 | 0.50 |
| H-D-iGlu-Trp-Lys | 0.24 | 0.46 |
| Leu-D-Glu-D-Trp-OH | 0.35 | 0.62 |
| Leu-D-iGlu-D-Trp-OH | 0.27 | 0.57 |

EXAMPLE 3

The biological effect of the D-iGlu-D-Trp (iDD) was studied in Balb/c mice. Splenic cells of the mice were suspended in RPMI 1640 medium with 2 ml glutamine and 5% inactive fetal serum, and then dispensed into flat-bottomed plates 100 μl, 200,000 cells, per well. The preparation under study was added at the beginning of the culture. Concavalin A was used as a mitogen, in a final concentration of 2 μg per well. The plates were incubated at 37° C. and in 5% $CO_2$ for 48 h. 3H-thymidine was incorporated into the cells in the amount of 5 μg/ml, 24 h prior to the end of the culture. Proliferation of the cells was measured with the use of a scintillation c-counter and expressed in counts per minute (CPM). The results are shown in Table 2.

TABLE 2

| | CPMI* Preparation dose (μcg/ml) | | | |
|---|---|---|---|---|
| Preparation | 1 | 5 | 10 | 20 |
| D-iGlu-D-Trp | 68590 | 63428 | 20043 | 13222 |
| Control | | 61467 | | |

*average value of three measurements

It can be seen that the spleen cells from mice treated with the peptide (iDD) showed a decrease in proliferative activity over cells from control mice.

EXAMPLE 4

The effect of peptides of the present invention on a population of hemopoietic progenitors was studied by testing for colony formation by hemopoietic stem cells in spleens of irradiated mice.

a) Treatment of intact bone marrow cells with the peptide H-D-Glu-D-Trp-Y in vitro.

Intact bone marrow cells were incubated at 37° C. for 1 hour with different concentrations of the peptide ranging from 0.0025 to 10 μg/ml. The suspension was injected to lethally irradiated recipient mice. After 8 days the animals were killed and spleen colonies were counted. The results are presented in Table 3.

TABLE 3

| Peptide dose, μg/ml | Thymocytes, $2 \times 10^7$ cells | Colony count |
|---|---|---|
| Control | − | 8,0 ± 0,6 |
| 0,0025 | − | 5,7 ± 0,5 |
| 0,005 | − | 5,4 ± 0,7 |
| 0,01 | − | 4,7 ± 0,3 |
| 0,02 | − | 2,8 ± 0,4 |
| 0,02 | + | 9,2 ± 0,2 |
| 0,05 | − | 3,0 ± 0,5 |
| 0,1 | − | 2,6 ± 0,6 |
| 0,2 | − | 3,0 ± 0,3 |
| 0,5 | − | 3,0 ± 0,6 |
| 1,0 | − | 2,4 ± 0,4 |
| 5,0 | − | 3,4 ± 0,5 |
| 10,0 | − | 3,0 ± 0,5 |

*$P < 0.05$ calculated relative to control

As the data illustrate, the incubation of bone marrow cells with the peptide in concentrations ranging from 0.0025 to 0.01 μg/ml reduced the colony yield by about 30–40%, the peptide in concentrations of 0.02–10 μg/ml suppressed the growth of colonies by more than 60%. In one of the groups mice received injections of thymocytes along with injections of bone marrow cells treated with the peptide (0.02 μg/ml). In that case, suppression of colony growth was negated, which showed that the peptide affected regulatory cells, which also participated in spleen colony formation, rather than directly hemopoietic progenitor cells.

b) Treatment of intact bone marrow cells with the peptide iDD in vitro.

The treatment was carried out as described above in Example 4(a). The results obtained are shown in Table 4.

TABLE 4

| Peptide dose, μg/ml | Thymocytes, $2 \times 10^7$ cells | Colony count |
|---|---|---|
| Control | − | 9,0 ± 0,6 |
| 0,02 | − | 3,6 ± 0,5 |
| 0,1 | − | 4,4 ± 0,5 |
| 1,0 | − | 4,3 ± 0,3 |
| 10,0 | − | 4,3 ± 0,1 |
| 10,0 | + | 8,7 ± 0,4 |
| 20,0 | − | 3,9 ± 0,4 |

*$P < 0.05$ calculated relative to control

As indicated in Table 4 the number of spleen colonies was decreased by more than 50% in the presence of the peptide.

c) Treatment of intact bone marrow cells with the peptide H-D-Glu-D-Trp-Y in vivo.

The peptide was injected intraperitoneally (IP) at different concentrations to intact mice. After two hours, one day, or two days the animals were killed. The bone marrow from the animals was taken to prepare a suspension of marrow cells, which was injected to lethally irradiated (8.5 Gy) mice. Along with the bone marrow, the recipients received injections of thymocytes. After 9 days, spleen colonies were counted. As the previous results suggested that the optimal peptide dose may be 0.02 μg/ml, this dose was used for all mice. The results are illustrated in Table 5.

TABLE 5

| Group | Colony count | CFU-S count |
|---|---|---|
| Control | 10,7 ± 0,5 | 2436 |
| Peptide, 2 hours before | 6,9 ± 0,8 | 1325 |
| Peptide, 1 day before | 5,9 ± 0,6 | 1074 |
| Peptide, 2 days before | 3,9 ± 0,5 | 728 |
| Peptide, 2 days before + thymocytes | 7,1 ± 0,7 | |

According to the data, the peptide injections to marrow donor mice lowered the number of exocolonies on spleens and reduced the CFU-S pool, with maximal inhibition observed two days after the peptide injection. An additional injection of thymocytes nullified the inhibiting effect. The cell compositions of bone marrow, thymus, and spleen cells in mice after the peptide injections were analyzed. The bone marrow cell count was found to be somewhat lower in the peptide treated group than in the control. In the thymus, the number of cells per mg of organ weight remained unchanged, and in the spleen it decreased. Control mice had $28.0 \times 10^7 \pm 3.0$ cells per mg, while those treated with the peptide had $18.2 \times 10^7$ cells per mg.

d) Treatment of intact bone marrow cells with the peptide iDD in vivo

The treatment was performed as described in Example 4(c). The results obtained are summarised in Table 6.

TABLE 6

| Group | Colony count | CFU-S count |
|---|---|---|
| Control | 10,7 ± 0,5 | 2436 |
| Peptide, 2 hours before | 6,6 ± 0,5 | 917 |
| Peptide, 1 day before | 4,7 ± 0,6 | 653 |
| Peptide, 2 days before | 6,0 ± 0,9 | 1098 |
| Peptide, 2 days before + thymocytes | 9,4 ± 0,9 | |

According to the data, the inhibiting effect of the peptide on the CFU-S population of bone marrow and the colony forming activity was observed as early as two hours after the peptide injection to mice and persisted for 2 days. Thymocytes nullified the effect of the peptide.

EXAMPLE 5

The mechanism of the inhibiting effect of the peptide on hemopoiesis was studied using the "thymidine suicide" test. The method provides an accurate measurement of the percentage of dividing cells (in the S-phase of the cell cycle). A bone marrow suspension is incubated with 3H-thymidine, which kills cells in the S-phase. Since the killed cells do not form colonies, one can determine the proliferation rate in a sample by comparing the difference between the number of spleen colonies in intact bone marrow cells with bone marrow cells treated with 3H-thymidine.

The first series of experiments investigated the effect of the peptide on CFU-S proliferation. Such an assay can not be done with intact marrow since the progenitors proliferate very poorly (0 to 15% in a cycle) in intact bone marrow. Consequently, as a source of CFU-S, "boosted" bone marrow was used containing at least 40% proliferating cells. "Boosted" bone marrow was obtained from mouse bone marrow on the 7th day following radiation with a dose of 4 Gy. Donor mice were irradiated with this dose and 5 or 6 days later they received iDD. On day 7 following the irradiation, the bone marrow was examined for the percentage of dividing cells, i.e. the iDD treatment lasted 1 or 2 days. According to the results obtained, when injected two days before the extraction of bone marrow, the peptide inhibited the proliferation so that the percentage of dividing cells was even lower than in intact subjects. When the peptide was injected one day before bone marrow was taken, no effect was observed (Table 7).

Thus, the data suggest that the peptide effect on CFU-S is due to its ability to suppress proliferation. Two days after the peptide administration, the number of CFU in S-phase of cell cycle diminishes in bone marrow.

Table 7 illustrates the effect of the peptide on cell proliferation in irradiated (4 Gy) bone marrow.

TABLE 7

| Group | Mice, n | Average colony count* | % CFU-S in S-phase |
|---|---|---|---|
| intact control | 20 | 10,5 ± 0,4 | |
| the same + $^3$H | 20 | 8,8 ± 0,5 | 10,5 |
| Irradiation | 20 | 2,0 ± 0,3 | |
| the same + $^3$H | 20 | 0,9 ± 0,1 | 55,0 |
| iDD, 2 days | 15 | 3,5 ± 0,2 | |
| the same + $^3$H | 15 | 2,8 ± 0,2 | 5,8 |
| iDD, 1 day | 15 | 8,3 ± 0,4 | |
| the same + $^3$H | 15 | 5,8 ± 0,5 | 50,6 |

*colony count is given per $10^5$ injected bone marrow cells

EXAMPLE 6

The effect of H-A-D-Trp-Y, where A is D-Glu or D-iGlu and Y is OH or a substituted amide, on protection and reconstitution of the population of hemopoietic progenitor cells in cytopenias of different origin was studied.

a) Protection and reconstitution of hemopoietic progenitor cells subjected to ionising radiation Ionising radiation was used to deplete bone marrow. Donor mice were irradiated at a dose of 4 Gy. For each of the two peptides, 10 μg/kg was injected intraperitoneally 1 hour, 1 day or 2 days before the irradiation (groups of 12 mice each). Bone marrow was taken from femoral bones 8 days after the irradiation. Eight days generally marks the beginning of an exponential reconstitution of both the total number of cells and the population of hemopoietic progenitors in the bone marrow, which were depleted as a result of irradiation.

On the 8th day a sharp statistically significant increase was recorded in the hemopoietic progenitor cells count in the bone marrow of the mice irradiated in the dose of 4 Gy who had received the peptide 2 days before the irradiation. The CFU-S content in the bone marrow of mice irradiated in the dose of 4 Gy and treated with the peptide are shown in Table 8.

TABLE 8

| Group | Mice, n | CFU-S count per femur |
|---|---|---|
| Control (4 Gy) | 12 | 401 ± 48 |
| H-D-Glu-D-Trp-OH - 2 days | 12 | 955 ± 93* |
| H-D-Glu-D-Trp-OH - 1 day | 12 | 780 ± 92* |
| H-D-Glu-D-Trp-OH - 1 hour | 12 | 450 ± 95 |
| H-D-iGlu-D-Trp-OH - 2 days | 12 | 677 ± 49* |
| H-D-iGlu-D-Trp-OH - 1 day | 12 | 324 ± 63 |
| H-D-iGlu-D-Trp-OH - 1 hour | 12 | 394 ± 57 |

*p < 0.05

The reconstitution of caryocyte numbers and that of hemopoietic progenitors was studied in femoral marrow after irradiation in the dose of 4 Gy and the peptide injection. The test was performed in 12 groups of mice, 6 animals each, and lasted 14 days. Intraperitoneal injections of the peptide in a dose of 10 μg/kg were made 1 day and 2 days before the irradiation. The results are summarised in Table

9.

TABLE 9

| Days after irradiation | 4 Gy | Caryocyte count × $10^6$ | | |
|---|---|---|---|---|
| | | H-D-Glu-D-Trp-OH | | H-D-iGlu-D-Trp-OH |
| | | 2 days | 1 day | 2 days |
| 4 | 9,0 ± 0,3 | 8,5 ± 0,5 | 8,0 ± 0,7 | 12,8 ± 0,9 |
| 7 | 10,6 ± 0,8 | 20,0 ± 0,7 | 16,4 ± 0,7 | 21,3 ± 2,1 |
| 11 | 17,0 ± 0,6 | 23,0 ± 1,9 | 16,0 ± 1,3 | 17,3 ± 1,0 |
| 14 | 17,9 ± 1,2 | 24,5 ± 0,9 | 15,0 ±0,6 | 20,5 ± 0,5 |

*p < 0.05

According to the test results, peptide injections made 2 days before irradiation markedly enhanced reconstitution of the number of cells in bone marrow: the caryocyte count reached the level of intact control already by the 7th day and, moreover, in the presence of H-D-iGlu-D-Trp-OH, the growth continued until the 14th day.

b) Protection and reconstitution of hemopoietic progenitor cells subjected to cytostatic cytosar Another agent that depletes the hemopoietic system, the cytostatic cytosar, was injected three times, once a day, at every 24 hours. Mice were divided into two groups of 12 animals each. The peptide, 10 μg/kg, was injected intraperitoneally three times, every two hours after the second cytosar injection. The animals were killed 3 hours after the last cytosar injection, and their femoral marrow was examined for caryocyte and CFU-S counts. Table 10 presents the data.

TABLE 10

| Group | Caryocytes | CFU-S |
|---|---|---|
| cytosar | 7,5 ± 0,4 × $10^6$ | 178,0 ± 27 |
| cytosar + peptide | 6,4 ± 0,3 × $10^6$ | 300,0 ± 34* |

*p < 0.05

It was found that in the presence of the peptide, which does not influence the caryocyte content in bone marrow, the viability of hemopoietic progenitors was 70% higher than in control.

The results of the study of the peptide effect on reconstitution of hemopoietic progenitors after their exposure to destructive factors (irradiation, cytostatics) show that the peptide, as an immunosuppressor, helps intensive reconstitution of the pool of hemopoietic progenitors (CFU-S) when injected prior to the exposure to the harmful factors, i.e. the peptide protects against destruction. This is probably due to the fact that the action of harmful factors (radiation, cytostatics) takes place when the hemopoietic progenitors are in $G_0$-phase ("at rest") (Example 5) being most resistant to the action of different damaging agents.

EXAMPLE 7

A comparative study was carried out on the effects of iDD and cyclosporin on the viability or "taking" of an allogenic bone marrow.

The effects of iDD and cyclosporin A were compared under the following conditions. Cyclosporin A was administered subcutaneously as a solution in olive oil at a dose of 25 mg/kg and iDD was administered intraperitoneally at a dose of 10 μg/kg. The preparations were administered daily for the first 5 days after transplantation of bone marrow transplants of donor mice C57B1 to lethally irradiated recipient mice Fl (CBA×C57Bl), starting from the 1st hour after the transplantation. The number of formed spleen colonies (a measure which characterizes the degree of transplant taking) was 3–2.5 times more in mice which were administered the preparation than in control subjects. Without the immunosuppression therapy, the percentage of CFU-S taking root was as little as 17%, while with the use of cyclosporin or iDD the value was 50 or 43%, respectively (Table 11). It is important to note that the iDD was administered at a dose that was several magnitudes lower than that for cyclosporin A.

TABLE 11

| Donor | Recipient | Mice, n | Average colony count | CFU-S taking root, % |
|---|---|---|---|---|
| F1 | F1 | 15 | 9,8 ± 0,4 | 100 |
| C57B1 | F1 | 15 | 1,7 ± 0,3* | 17,3 |
| C57B1 + cyclosporin | F1 | 15 | 5,0 ± 0,2 | 51 |
| C57B1 + iDD | F1 | 15 | 4,2 ± 0,3 | 43 |

*trustworthiness was calculated as applied to this group P < 0.05
-colony count is given per $10^5$ of injected bone marrow cells The survival data on the above described mice after 42 days is presented in Table 12.

TABLE 12

| Group* | Survived mice, % | MCL** |
|---|---|---|
| control | 50 | 14,3 |
| cyclosporin | 67 | 6,6 |
| iDD | 93 | 6,0 |

*Each group consisted of 15 mice
**Medium continuation of life

The results demonstrate that mice treated with iDD showed the greatest survival rate.

EXAMPLE 8

The effect of the peptide on a chronic "graft versus host reaction" (GVHR) was studied, using the model described by Bundic et al. (Exp. Immunol. 1995, 99, p.467). Chronic GVHR was induced in hybrid non-irradiated animals by injecting them twice with large amounts (100 mln) of spleen cells of one of the parents. The development of GVHR was observed for 21 days.

Recipients were (CBA×C57B1)F1 mice, and donors of spleen cells were mice of the strain C57B1. The preparation iDD was administered in the same dose (10 μg/kg/injection) as in the tests on transplantation of allogenic bone marrow. The five-day treatment course began 24 hours after the first injection of spleen cells and lasted three weeks. Control group mice received Medium 199 in the same amount and at the same time as test mice received the peptide. Each group consisted of 15 animals.

Indicators of the degree of GVHR development were animal weight and splenomegaly (as measured by the increase in recipient's spleen weight on day 21). The effectiveness of the preparation was assessed by splenomegaly suppression expressed in % to control (splenomegaly in the control group was taken for 100%). The interval between the first and the second injections of spleen cells was 7 days. It is seen from the results presented in the Table 13 that there was practically no weight loss throughout the experiment in the group of mice receiving iDD, whereas in the control group the weight loss was 3 g.

TABLE 13

| | Mouse weight, g Days after the first injection of spleen cells | | | |
|---|---|---|---|---|
| Group | 0 | 7 | 14 | 21 |
| Control | 22,3 ± 0,9 | 21,7 ± 0,8 | 18,3 ± 0,9 | 19,3 ± 1,1 |
| iDD | 22,6 ± 0,7 | 25,0 ± 0,6 | 23,3 ± 1,0 | 22,7 ± 0,9 |

In the control group, the survival was 80%, as compared to a survival rate of 100% in the test group. The time of the deaths (days 14 and 16) indicates that the reason for death was GVHR.

On day 21, a sharp increase in weight was recorded in 70% of control mice and 55% of test mice. As shown in Table 14, the degree of splenomegaly was calculated as the ratio of spleen weight in mg to body weight in grams. It was found that, using this method of administration and dosage, iDD did not eliminate GVHR completely but did reduce its development.

TABLE 14

| Splenomegaly under chronic GVHR | | | |
|---|---|---|---|
| Group | Mice, n | Splenomegaly, mg spleen per mg body weight | Splenomegaly suppression, % |
| Intact | 10 | 3,4 ± 0,3 | |
| Control | 15 | 12,6 ± 1,2 | |
| iDD | 15 | 10,2 ± 1,0 | 26% |

EXAMPLE 9

Transplantation of the bone marrow will prove effective if two main problems are solved. Firstly, conditions are to be provided for the transplanted cells to take root and go on functioning, and secondly the graft versus host reaction, GVHR, must be suppressed. The second problem may be solved with the transplantation of lesser amounts of the bone marrow as it is known that GVHR in mice is much weaker when less that 8 million allogenic bone marrow cells are transplanted. In this case, however, the regenerating effect on hemopoiesis may be low because of the insufficient amount of cells. A solution taught herein is use of a preparation that can promote the establishment of the bone marrow transplant and, at the same time, suppress the development of GVHR.

In a series of experiments, bone marrow cells (6 million) of one of the parents were transplanted to lethally irradiated recipient mice which were hybrids of the first generation. Transplantation of this amount generally does not cause a pronounced GVHR manifesting in the death of test animals. Generally, weight loss is observed and there is a small percent of deaths during the 42-day study.

A day after the bone marrow transplantation, test recipients began to receive therapy. Three schemes of therapy were used: (1) iDD, 10 μg/kg, ip, for 5 days running, with 2-day intervals, for 6 weeks (K+iDD); (2) before transplantation, bone marrow transplants were treated with iDD in vitro for 1 hour at 37° C., 0.2 μg per 2×10⁶ cells, without in vitro treatment with the preparation (iDD); and (3) bone marrow was pre-treated in vitro as described in scheme 2, followed by iDD therapy as in scheme 1 (iDD+iDD). Control subjects were mice that were transplanted with the bone marrow without any further therapy. These animals received ip injections of the solvent according to the same schedule.

Table 15 shows the and the state of hemopoiesis in lethally irradiated mice after transplantation of the allogenic bone marrow under the described therapeutic schemes.

TABLE 15

| Group | Caryocytes in brain, × 10⁶ | Caryocytes in blood, thousand/μl | Lymphocytes, % |
|---|---|---|---|
| Control | 22,1 + 0,7 | 1,7 + 0,3* | 3* |
| K + iDD | 30,7 + 0,3 | 3,8 + 0,3 | 19 |
| iDD | 21,0 + 0,9 | 4,2 + 0,3 | 21,5 |
| iDD + iDD | 26,5 + 1,6 | 5,2 + 0,6* | 40* |
| Intact | 27,3 + 0,8 | 5,4 + 1,0 | 43 |

*P < 0.005

The data shown in Table 15 illustrates that 6 weeks after the lethal irradiation and transplantation of allogenic bone marrow the cell composition of the bone marrow differed little from that in intact mice. The functional state of the organ is characterized by the indices of nucleated blood cells (NBC) and the percentage of lymphocytes among them. As one can see, the NBC count in control animals is 3 times as low as in intact ones. In the remaining test groups, NBC counts in treated mice do not differ substantially from those in intact animals. Furthermore, an almost complete absence of lymphocytes was observed in the peripheral blood of the control subjects. K+iDD and iDD increased the lymphcyte count 6–7 times, these figures, however, being only half of the normal lymphocyte content. Only with double action of iDD (in vitro and in vivo) was the lymphocyte percentage equal to that in intact animals by the 42nd day after bone marrow transplantation.

Thus, the use of the immunosuppressor after bone marrow transplantation or for in vitro treatment of the bone marrow improves the bone marrow transplant taking and further functioning.

EXAMPLE 10

The protective effect of the peptide (iDD) on hyperthermic bone marrow cells was studied.

Hyperthermia is used in the treatment of various cancer types. When treating leukosis, the damaged bone marrow cells are heated at approximately 41–42° C. in order to kill malignant cells as they are more sensitive to heat. However, some non-malignant stem cells may also be affected. Consequently, the ability of the iDD peptide to protect cells during hyperthermia was tested. A suspension of the bone marrow, previously incubated for 1 hour at 37° C. in the presence of iDD (0.2 μg/4×10⁶ cells), was heated for 30 minutes at 42° C. It was then diluted until the necessary concentration was reached and transplanted to the lethally radiated recipients. The quantity of the exogenous colonies in the spleen was determined on the ninth day. As shown in Table 16, whereas heating during 30 minutes decreases the survival of the control CFU-S to 52% (by 48%), then preliminary treatment with iDD increases the survival rate. The decrease of the colony formation under the action of iDD is not critical, because its colony-inhibiting action is reversible.

TABLE 16

Influence of Thymodepressin on the survival CFU-S after heating

| Group | Quantity of mice | Medium quantity of colonies | Survival of CFU-S, % |
|---|---|---|---|
| Control | 7 | 11.4 +/- 0.4 | 100 |
| Control + heating | 8 | 5.9 +/- 0.6 | 51.7 |
| iDD | 7 | 6.0 +/- 0.6 | 100 |
| iDD + heating | 7 | 6.9 +/- 0.6 | 115 |

EXAMPLE 11

Inhibition of the Mixed Lymphocyte Culture (MLC) Proliferation

The influence of the peptides of the invention on the proliferation of a mixed lymphocyte culture (MLC) was studied. The MLC experimental system is an in vitro analogue of the GVHD reaction.

Donor spleen cells from C57B1 mice (H-2d) were injected into recipient (CBA×C57B1) Fl mice. Bone marrow was removed from the recipient and cultured for 4 days. The cultured cells were separated into 3 test groups, one group was treated with iDD, one with the L-peptide H-Ele-Glu-Trp-OH and one was a control. Each test peptide was added in various concentrations. Each determination was done in triplicate. $^3$H-thymidine was added to each culture for 16 hours and the index of the proliferation of the cells was calculated.

The results shown in FIG. 1 demonstrate that H-Ile-Glu-Trp-OH in concentrations 1, 10, 20 µg/ml stimulates the proliferation of the allogenic lymphocytes, while at 0.1 µg/ml it exhibited negligible inhibition of the proliferation. In contrast, iDD added to the MLC in the concentrations of 10 and 20 µg/ml, significantly depresses the proliferation MLC (approximately by 50%). When both H-Ile-Glu-Trp-OH and iDD were added to MLC in equal concentrations, the effect of iDD was predominant, probably because of its higher affinity to lymphocyte receptors.

EXAMPLE 12

Clinical Studies

The peptide iDD was given to patients with cytopenias of immune origin and its effect on hemopoietic status was assessed using a number of immunological tests characterising both humoral and cellular immunity.

The iDD was administered 0.1 mg in a 1 ml dose intranasally (once or twice in divided doses) for 5 days. The regime was repeated after a two week interval. For patients receiving steroids and cytostatics, iDD was administered during the therapy or before the cytostatic treatment.

Results

In the period of a prolonged administration of iDD (5–6 courses) no toxic reactions, skin rash, disturbance of gastrointestinal function, central or peripheral nervous system, vascular, muscular or other adverse reactions were noted.

Physical examinations of patients before and after the treatment revealed no changes in the somatic status, which could be ascribed to the action of the test preparation.

The dynamics of biochemical indices—bilirubin, alanine and asparaginic transaminases, alkaline phosphatase, lactate dehydrogenase, glucose, carbamide, creatinine, uric acid, total protein, protein fractions, electrolytes—before and after 1–3 treatment courses revealed no changes associated with iDD administration. Changes in AP dynamics and ECG caused by iDD were not observed. No toxic manifestations, deviations of biochemical indices, or shifts on the part of the cardiovascular system were observed, not only after the first course but also after a series of iDD courses.

Practically all patients were refractory to treatment with average prednisolone doses. Though there was no clear evidence of compensation in hematograms, there was some evidence of the process stabilisation in the absence of a pronounced hemorrhagic syndrome in the patients.

Below are cited the examples of indices dynamics in some patients.

Patient A., born 1924. Diagnosis: immune three-line cytopenia since 1994. Treated with prednisolone and erythrocyte transfusions. Has not been treated with steroids since 3/96. iDD treatment since 12/96. Experienced aggravation after influenza—since 3/97 a sharp decrease in thrombocyte content, a moderate reduction of haemoglobin. Against the background of iDD treatment the patient tended to normalise—without administration of steroids the content of thrombocytes stopped falling (62 -51 -68 bln/l), haemoglobin content stabilised (106 g/l). Dynamics of leukocytes— 4.14.5 bln/l, lymphocytes—39–20%.

TABLE 17

| Cell Phenotype, subpopulation | % of cells, Normal | % of cells test sample | Absolute count, bln/1 | % of cells After iDD treatment | Absolute count, bln/1 after iDD |
|---|---|---|---|---|---|
| CD45 ++ CD14 – lymphocytes | | 33.2 | 1.6 | 34.8 | 0.9 |
| CD45 + CD14 – granulocytes | | 41.4 | | 48.5 | |
| CD45 + CD14 – monocytes | | 61 | | 3.3 | |
| CD3 + CD19 – T-lymphocytes | 62.8–85.0 | 78.9 | | | |
| CD3 – CD19 + B-lymphocytes | 7.1–23.3 | 12.7 | | | |
| CD4 + CD8 – T-helpers | 31.4–63.8 | 48.1 | 0.769 | 58.0 | 0.522 |
| CD4 – CD8 + T-Suppressers | 18.9–47.9 | 41.1 | 0.657 | 33.9 | 0.305 |
| CD4 + /CD8 + ratio | 0.7–3.3 | 1.2 | | 1.7 | |

TABLE 17-continued

| Cell Phenotype, subpopulation | % of cells, Normal | % of cells test sample | Absolute count, bln/l | % of cells After iDD treatment | Absolute count, bln/l after iDD |
|---|---|---|---|---|---|
| CD3 + HLA – DR+ activated T-lymphocytes | 2.8–17.3 | 24.3 | 0.388 | 27.9 | 0.251 |
| CD3 – CD16,56 + nat. killers | 4.8–26.7 | 10.3 | 0.164 | 12.0 | 0.108 |
| CD34 + stem cells | | 0 | | | |
| CD5 + T-cell. marker | | 90.9 | | | |

Table 17 shows that, while there is no pronounced dynamics of the relative indices, the absolute counts of CD45++ CD14-, CD4+CD8- and CD4-CD8+tend to decrease.

Patient K., 1915. D-s autoimmune haemolytic anaemia since 1992. Treated with steroid hormones, imuran. Since 2/97—imuran and iDD, with the halved dose of imuran due to bad tolerance. Stabilisation of the process was noted: haemoglobin content—100–107 g/l, reticulocytes—2.5–0.3%. Dynamics of leukocytes—5.6–5.1 bln/l, lymphocytes—30–21.5%.

TABLE 18

| Cell Phenotype, subpopulation | % of cells, Normal | % of cells test sample | Absolute count, bln/l | % of cells After iDD treatment | Absolute count, bln/l |
|---|---|---|---|---|---|
| CD45 ++ CD14 – lymphocytes | | 26.0 | 1.68 | 20.2 | 1.09 |
| CD45 + CD14 – granulocytes | | 55.8 | | 74.7 | |
| CD45 + CD14 – monocytes | | 5.3 | | 5.2 | |
| CD3 + CD19 – T-lymphocytes | 62.8–85.0 | 83.3 | | | |
| CD3 – CD19 + B-lymphocytes | 7.1–23.3 | 16.2 | | | |
| CD4 + CD8 – T-helpers | 31.4–63.8 | 36.3 | 0.614 | 36.1 | 0.393 |
| CD4 – CD8 + T-Suppressers | 18.9–47.9 | 44.5 | 0.712 | 46.8 | 0.510 |
| CD4 + /CD8 + ratio | 0.7–0.8 | | 0.8 | | |
| CD3 + HLA – DR+ activated T-lymphocytes | 2.8–17.3 | 15.1 | | | |
| CD3 – CD16,56 + nat. killers | 4.8–26.7 | 3.4 | 0.057 | 5.0 | 0.054 |
| CD34 + stem cells | | 0 | | | |
| CD5 + T-cell. marker | | 83.9 | | | |

Table 18 shows the tendency towards a decrease of the absolute counts of CD45++CD14-, CD4+CD8- and CD4-CD8+lymphocytes.

EXAMPLE 13

The peptide's effect in a chronic lymphocyte-induced graft-versus-host reaction (GVHR) was studied, using a model which is a modification of the model used in Example 8.

Recipient (CBA×C57 B1) Fl mice were irradiated with the dose of 6 Gy. Two hours after irradiation they were intravenously injected with 6 mln lymphocytes from mesenteric lymph nodes of C57B1 donor mice. 24 hours after the cell injection the recipients received the peptide dissolved in Medium 199, in doses or either 10 μ/kg, 100 μ/kg, or 1000 μ/kg (10 animals per group). The peptide was injected intraperitoneally once daily, 5 days a week, until day 21, for a total of 14 injections. Control mice received Medium 199 according to the same scheme.

Figure 2:
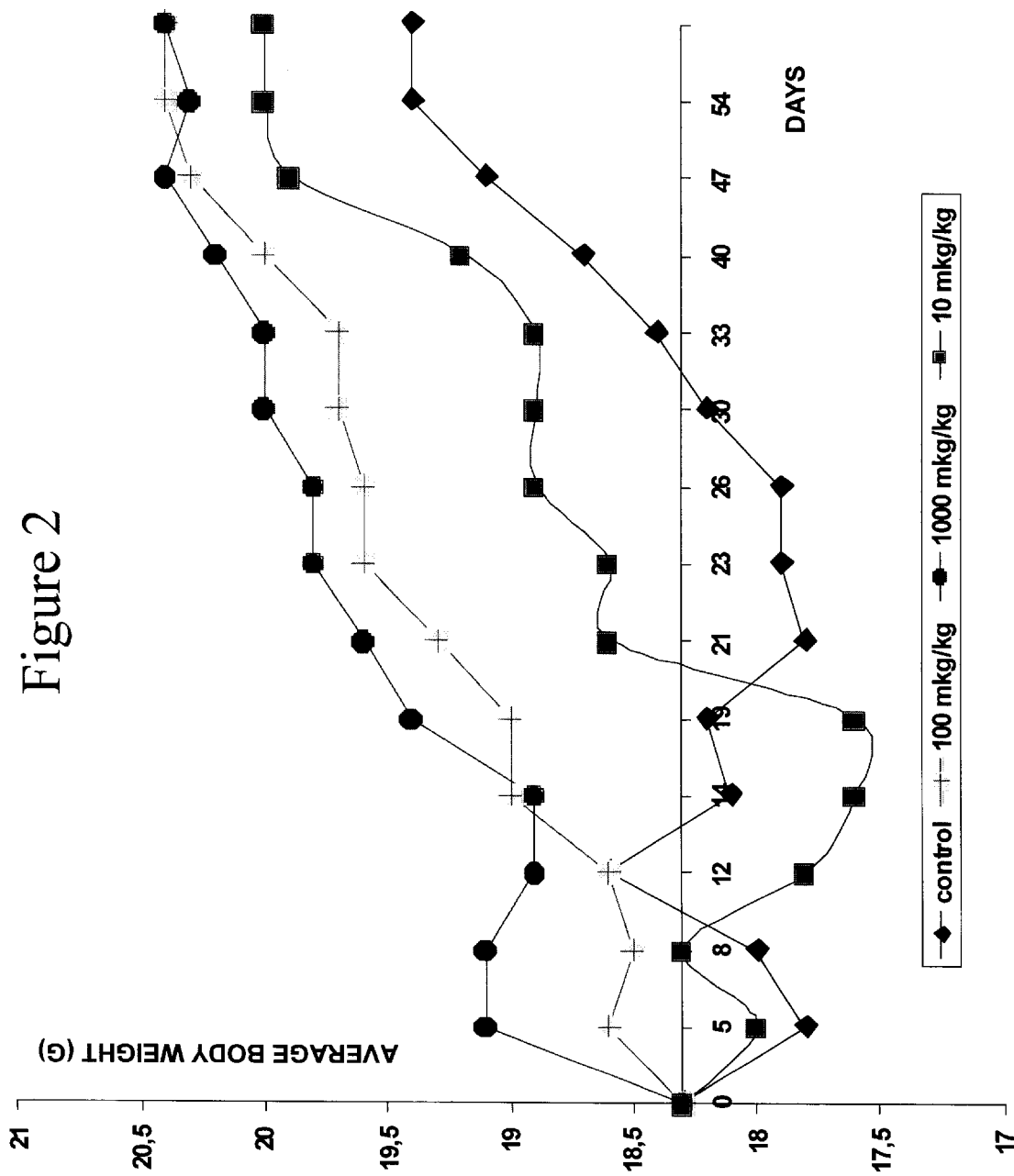
FIG. 2 is a graph showing the effect of a peptide of the invention on weight gain, contemporaneous with irradiation.

Indicators of the degree of GVHR development were animal weight and lymphocyte and leukocyte count. The animals were weighed every 3 days. On day 14 and day 28 lymphocyte and leukocyte count were determined using peripheral blood. The results are presented in FIG. 2 and Tables 19, 20, and 21.

As shown in Table 21, mice treated with the peptide showed increased survival rates over the control mice. As shown in Table 19 and FIG. 2, over the course of the injection regimen (day 1 to day 21), mice treated with the peptide in 100 μ/kg and 1000 μ/kg doses exhibited fairly consistent weight gain, while control mice and mice receiving 10 μ/kg of the peptide generally exhibited weight loss. Table 20 shows that the lymphocyte and leukocyte counts of the mice receiving the peptide during radiation therapy were significantly higher than the same counts for the control mice, indicating that the peptide may play a role in protecting cells of the hematopoietic and immune systems in the animals during radiation therapy.

Neither the survival rates nor the blood analyses of the test animals revealed any dose dependence. However, having regard to the differences in weight gains, these preliminary results suggest that a dose of 100 μ/kg may be optimal in the discussed model.

It will be appreciated that various changes may be made within the spirit of the described invention, and all such changes are within the scope of the appended claims.

All publications, patents and patent applications referred to herein are hereby incorporated by reference in their entirety to the same extent as if each individual publication, patent or patent application was specifically and individually indicated to be incorporated by reference in its entirety.

TABLE 19

| Dose of the Peptide | Animal Weight, grams Initial average weight- 18.3 g Day | | | | | | | | | | | | |
|---|---|---|---|---|---|---|---|---|---|---|---|---|---|
| | 5 | 8 | 12 | 14 | 19 | 21 | 23 | 26 | 30 | 33 | 40 | 47 | 54 | 60 |
| Control | 17,8 | 18,0 | 18,6 | 18,1 | 18,2 | 17,8 | 17,9 | 17,9 | 18,2 | 18,4 | 18,7 | 19,1 | 19,4 | 19,4 |
| 10 μ/kg | 18,0 | 18,3 | 18,3 | 17,8 | 17,6 | 17,8 | 18,6 | 18,9 | 18,9 | 18,9 | 19,2 | 19,9 | 20,0 | 20,0 |
| 100 μ/kg | 18,6 | 18,5 | 18,6 | 19,0 | 19,0 | 19,3 | 19,6 | 19,6 | 19,7 | 19,7 | 20,0 | 20,3 | 20,4 | 20,4 |
| 1000 μ/kg | 19,1 | 19,1 | 18,9 | 18,9 | 19,4 | 19,6 | 19,8 | 19,8 | 20,0 | 20,0 | 20,2 | 20,5 | 20,1 | 20,4 |

TABLE 20

THE EFFECT OF THE PEPTIDE ON LEUKOCYTE AND LYMPHOCYTE DYNAMICS

| | Group | | | |
|---|---|---|---|---|
| | Leukocytes (mln/L) | | Lymphocytes % (mln/L) | |
| | Day 14 | Day 28 | Day 14 | Day 28 |
| Control | 2,6 ± 0,3 | 7,4 ± 0,7 | 17 ± 1,5 (0,442) | 14,6 ± 1,3 (1,080) |
| Thymodepressin 10 μ/kg | 3,4 ± 0,6 | 1,4 ± 1,0 | 34,2 ± 1,1 (1,136) | 24,4 ± 2,9 (2,782) |
| 100 μ/kg | 4,3 ± 0,5 | 7,8 ± 0,8 | 39,0 ± 2,2 (1,677) | 34,2 ± 1,8 (2,668) |
| 1000 μ/kg | 3,7 ± 0,5 | 7,9 ± 0,6 | 27,3 ± 3,6 (1,010) | 32,0 ± 1,9 (2,528) |
| Intact animals | 9,3 ± 0,3 | 10,0 ± 0,3 | 42,0 ± 2,1 (3,906) | 41,3 ± 1,4 (4,130) |

TABLE 21

Survival of mice after 60 days

| Dose of Thymodepressin | Mice, n | Survival | Survival (%) |
|---|---|---|---|
| Control | 10 | 6 | 60 |
| 10 μ/kg | 10 | 9 | 90 |
| 100 μ/kg | 10 | 9 | 90 |
| 1000 μ/kg | 10 | 8 | 80 |

It will be appreciated that various changes may be made within the spirit of the described invention, and all such changes are within the scope of the appended claims.

All publications, patents and patent applications referred to herein are hereby incorporated by reference in their entirety to the same extent as if each individual publication, patent or patent application was specifically and individually indicated to be incorporated by reference in its entirety.

I claim:

1. A method of inhibiting cell proliferation comprising administering an effective amount of a peptide of the formula I:

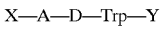

$$X\text{—}A\text{—}D\text{—}Trp\text{—}Y \qquad (I)$$

wherein X is selected from the group comprising hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, and ξ-aminocaproic acid; A is selected from the group comprising D-glutamic acid and D-iso-glutamic acid; and Y is selected from the group comprising glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tyrptophan, γ-aminobutyric acid, ξ-aminocaproic acid, hydroxyl and an amide group, to a person or cell in need thereof.

2. A method according to claim 1 wherein X is hydrogen, A is D-i-glutamic acid, and Y is selected from the group consisting of hydroxyl and an amide group substituted with a C1–C3 alkyl group.

3. A method according to claim 1 wherein the peptide has the sequence H-D-iGlu-Trp-OH.

4. A method according to claim 1 wherein the peptide is administered in a dose from about 1 μg to about 10 g per kilogram of weight of the patient.

5. A method according to claim 1 wherein the peptide is administered in dose from about 0.1 g to about 10 g per kilogram of weight of the patient.

6. A method according to claim 1 wherein cell proliferation is hematopoietic cell proliferation.

7. A method according to claim 1 wherein cell proliferation is immune system cell proliferation.

* * * * *

UNITED STATES PATENT AND TRADEMARK OFFICE
CERTIFICATE OF CORRECTION

PATENT NO.       : 6,103,699
APPLICATION NO. : 09/032550
DATED            : August 15, 2000
INVENTOR(S)      : Vladislav I. Deigin and Andrei Marxovich Korotkov It is certified that error appears in the above-identified patent and that said Letters Patent is hereby corrected as shown below:

On Title Page, Item (57)
Abstract "D-iso-glutamic acid" should read -- D-γ-glutamic acid --;

Figure 1 "iDD" should read -- γDD --;

Column 2, lines 13 "D-iso-glutamic acid; D-iGlu" should read -- D-γ-glutamic acid (D-γGlu) --, 20 "H-D-iGlu-Trp-OH" should read -- H-D-γGlu-Trp-OH --;

Column 3, lines 12 "iGlu—iso-glutamic acid" should read -- γGlu—γ-glutamic acid --, 25 "D-iso-glutamic acid" should read -- D-γ-glutamic acid --, 32 "D-iso-glutamic acid" should read -- D-γ-glutamic acid --, 46 "H-D-iGlu-Trp-OH (also referred to as "iDD")" should read -- H-D-γGlu-Trp-OH (also referred to as "γDD") --;

Column 4, lines 23 "Boc-iGlu" should read -- Boc-γGlu --, 25 "isoglutamyl" should read -- γglutamyl --;

Column 6, lines 10 "H-D-iGlu-Trp-OH (iDD)" should read -- H-D-γGlu-Trp-OH (γDD) --, 26 "Boc-iD-Glu-D-Trp-OH" should read -- Boc-D-γGlu-D-Trp-OH --, 49 "Boc-D-iGlu-Trp-OH" should read -- Boc-D-γGlu-Trp-OH --, 51 "H-D-iGlu-D-Trp-OH" should read -- H-D-γGlu-D-Trp-OH --, 53 "Boc-D-iGlu-Trp-OH" should read -- Boc-D-γGlu-Trp-OH --, 60 "H-D-iGlu-Trp-OH" should read -- H-D-γGlu-Trp-OH --, 64 "H-D-iGlu-Trp-OH" should read -- H-D-γGlu-Trp-OH --, 65 "$C_{16}H_{20}N_3O_5$" should read -- $C_{16}H_{19}N_3O_5$ --, 66 "334.35" should read -- 333.34 --;

Column 7, Table 1 "H-D-iGlu-Trp-OH" should read -- H-D-γGlu-Trp-OH --, "H-L-iGlu-D-Trp-OH" should read -- H-L-γGlu-D-Trp-OH --, "Ala-D-iGlu-D-Trp-OH" should read -- Ala-D-γGlu-D-Trp-OH --, "ζ-aminocaproyl-D-iGlu-D-Trp-OH" should read -- ζ-aminocaproyl-D-γGlu-D-Trp-OH --, "H-D-iGlu-Trp-Lys" should read -- H-D-γGlu-Trp-Lys --, "Leu-D-iGlu-D-Trp-OH" should read -- Leu-D-γGlu-D-Trp-OH --;

Column 7, lines 32 "D-iGlu-D-Trp (iDD)" should read -- D-γGlu-D-Trp (γDD) --, 56 "(iDD)" should read -- (γDD) --;

Column 7, Table 2 "D-iGlu-D-Trp" should read -- D-γGlu-D-Trp --;

Column 8, line 36 "iDD" should read -- γDD --;

UNITED STATES PATENT AND TRADEMARK OFFICE
CERTIFICATE OF CORRECTION

PATENT NO. : 6,103,699
APPLICATION NO. : 09/032550
DATED : August 15, 2000
INVENTOR(S) : Vladislav I. Deigin and Andrei Marxovich Korotkov It is certified that error appears in the above-identified patent and that said Letters Patent is hereby corrected as shown below:

Column 9, lines 25 "iDD" should read -- $\gamma$DD --, 62 "iDD" should read -- $\gamma$DD -- and 64 "iDD" should read -- $\gamma$DD --;

Column 10, Table 7 "iDD, 2 days" should read -- $\gamma$DD, 2 days -- and "iDD, 1 day" should read -- $\gamma$DD, 1 day --;

Column 10, line 26 "D-iGlu" should read -- D-$\gamma$Glu --;

Column 10, Table 8 "H-D-iGlu-D-Trp-OH - 2 days" should read -- H-D-$\gamma$Glu-D-Trp-OH - 2 days --,"H-D-iGlu-D-Trp-OH - 1 day" should read -- H-D-$\gamma$Glu-D-Trp-OH - 1 day --, "H-D-iGlu-D-Trp-OH - 1 hour" should read -- H-D-$\gamma$Glu-D-Trp-OH - 1 hour --;

Column 11, Table 9 "H-D-iGlu-D-Trp-OH" should read -- H-D-$\gamma$Glu-D-Trp-OH --;

Column 11, lines 19 "H-D-iGlu-D-Trp-OH" should read -- H-D-$\gamma$Glu-D-Trp-OH --, 56 "iDD" should read -- $\gamma$DD --, 59 "iDD" should read -- $\gamma$DD --, 62 "iDD" should read -- $\gamma$DD --;

Column 12, lines 6, 7, 35, 50, 66 "iDD" should read -- $\gamma$DD --;

Column 12, Table 11 "C57Bl + iDD" should read -- C57Bl + $\gamma$DD --;

Column 12, Table 12 "iDD" should read -- $\gamma$DD --;

Column 13, Table 13 "iDD" should read -- $\gamma$DD --;

Column 13, lines 20 "iDD" should read -- $\gamma$DD --, 57 "iDD" should read -- $\gamma$DD --, 58 "(K + iDD)" should read -- (K + $\gamma$DD) --, 61 "(iDD)" should read -- ($\gamma$DD) --, 63 "iDD" should read -- $\gamma$DD --, 63 "(iDD + iDD)" should read -- ($\gamma$DD + $\gamma$DD) --;

Column 13, Table 14 "iDD" should read -- $\gamma$DD --;

Column 14, Table 15 "K + iDD" should read -- K + $\gamma$DD --, "iDD" should read -- $\gamma$DD --, "iDD + iDD" should read -- $\gamma$DD + $\gamma$DD --;

Column 14, lines 29 "K + iDD and iDD" should read -- K + $\gamma$DD and $\gamma$DD --, 32 "iDD" should read -- $\gamma$DD --, 46 "(iDD)" should read -- ($\gamma$DD) --, 54 "iDD" should read -- $\gamma$DD --, 57 "iDD" should read -- $\gamma$DD --, 64 "iDD" should read -- $\gamma$DD --, 66 "iDD" should read -- $\gamma$DD --;

UNITED STATES PATENT AND TRADEMARK OFFICE
CERTIFICATE OF CORRECTION

PATENT NO. : 6,103,699
APPLICATION NO. : 09/032550
DATED : August 15, 2000
INVENTOR(S) : Vladislav I. Deigin and Andrei Marxovich Korotkov It is certified that error appears in the above-identified patent and that said Letters Patent is hereby corrected as shown below:

Column 15, Table 16 "iDD" should read -- γDD --, "iDD + heating" should read -- γDD + heating --;

Column 15, lines 25, 35, 38, 39, 43 "iDD" should read -- γDD --;

Column 16, lines 3, 6, 10, 22, 23, 26, 38, 41 "iDD" should read -- γDD --;

Column 16 and 17, Table 17 "After iDD" and "after iDD" should read -- After γDD -- and -- after γDD -- respectively;

Column 17, line 21 "iDD" should read -- γDD --;

Column 17, Table 18 "After iDD" should read -- After γDD --.

Claim 1, Column 20, line 38, "D-iso-glutamic acid" should read --D-γ-glutamic acid--;

Claim 2, Column 20, line 49, "D-i-glutamic acid" should read --D-γ-glutamic acid--;

Claim 3, Column 20, line 54, "H-D-iGlu-Trp-OH" should read --H-D-γGlu-Trp-OH--

Signed and Sealed this

Nineteenth Day of December, 2006

JON W. DUDAS
*Director of the United States Patent and Trademark Office*